United States Patent [19]
Bent

[11] 4,199,160
[45] Apr. 22, 1980

[54] SURGICAL DRILL CHUCK
[75] Inventor: John H. Bent, Costa Mesa, Calif.
[73] Assignee: Minnesota Mining and Manufacturing Company, St. Paul, Minn.
[21] Appl. No.: 906,858
[22] Filed: May 17, 1978
[51] Int. Cl.² ............................................. B23B 31/10
[52] U.S. Cl. ..................... 279/30; 433/127; 279/1 B; 279/75
[58] Field of Search ............... 279/1 B, 30, 22, 74, 279/75; 32/26

[56] References Cited
U.S. PATENT DOCUMENTS 1,174,997  3/1916  Lackner ............................ 279/74
3,674,281  7/1972  Hedrick ............................ 279/30

FOREIGN PATENT DOCUMENTS 40692  8/1932  France ............................ 32/26

*Primary Examiner*—Z. R. Bilinsky
*Attorney, Agent, or Firm*—Cruzan Alexander; Donald M. Sell; Edward T. Okubo

[57] ABSTRACT

A quick release drill chuck for surgical and dental instruments, particularly high speed drills powered by rotary air motors, is disclosed. The chuck engages the shafts of drills or burs and is actuated without the use of additional tools while providing a self-locking feature to insure against inadvertent loosening of the chuck.

1 Claim, 2 Drawing Figures

SURGICAL DRILL CHUCK

BACKGROUND OF THE INVENTION

The present invention relates to a quick release chuck for surgical and dental instruments, particularly for high speed instruments powered by rotary air motors. The chuck engages the shafts of drills or burs and is actuated without the use of additional tools. Another advantage of the present invention is realized through incorporation of a self-locking feature which requires a minimum amount of torque to activate and provides insurance against inadvertent loosening of the locking mechanism.

Small hand-held high-speed drills having substantial torque are necessary in the performance of bone surgery. Although small and light weight so as to minimize surgeon fatique during lengthy surgical procedures, the devices are designed and manufactured with utmost precision for minimum unbalance and vibration at high rotational speeds. While the drills used by surgeons and dentists are somewhat similar in size and purpose and use many of the same drills and burs, the instruments are generally different. Dental drills are usually smaller in size, have a higher rotational speed and require less torque and, hence, usually use an air turbine for power. While surgical drills also use air turbines, many, including those for which the present device is intended, use an air motor, which provides greater torque and slightly lower velocity. The greater torque, in turn, places more stringent requirements for drill and bur engagement which are not met by the many surgical drill chucks which have evolved from dental drill designs.

During the course of a surgical operation, it is necessary for the surgeon to frequently remove and replace the drill or bur with a different sized tool or merely to replace one that has become dulled. Minimization of time is important and frequently critical during a surgical procedure. Frequent replacement of dulled burs with new sharp burs can speed bone cutting but, in terms of overall time, only if the burs can be replaced quickly. The use of wrenches, keys or other tools to implement bur replacement is undesirable because such use of tools not only delays the replacement but frequently such tools can be misplaced causing even longer intolerable delays. Almost all modern surgical drills accommodate quick release chucks which can be actuated without the use of auxiliary tools. The fact that these quick release chucks are available in countless different designs would appear to confirm that design deficiencies still exist.

Early dental drills used a simple chuck mechanism which was merely a resilient plastic or rubber sleeve. When the sleeve wore to the point where excessive slippage occurred, it was replaced. Obviously, such devices would be impractical for surgical usage because of the need for greater torque and greater precision in surgical procedure. Slippage would be intolerable. For similar reasons, the resilient slotted metal chuck of Thorburn U.S. Pat. No. 3,869,796 would be acceptable for dental purposes but not for surgical usage.

Lieb U.S. Pat. No. 3,893,242 describes a compact air-turbine powered dental hand piece which requires the use of a novel auxiliary wrench for changes of burs. As previously mentioned, the use of such wrenches is extremely inconvenient for surgical use.

Hagen U.S. Pat. No. 3,835,858 and Nordin U.S. Pat. No. 3,867,943, both describe surgical drills which require interchange of the entire hand piece containing not only the cutting bur but also support bearings, clutch, housing, etc. While the use of a bur guard and support is obviously necessary with certain long shafted burs, replacement of such complex components each and every time that the burs become dulled is excessively expensive. In addition, while these devices have the advantage that the burs can be changed while the motor is rotating, they have the disadvantage that it is difficult to replace the hand piece when the motor is not rotating. Further, the snap action closure is a potential source of trouble since the hand piece can be easily and inadvertently dislodged during usage.

Shea U.S. Pat. No. 4,007,528 describes another common means of bur shank engagement with a plurality of spherical detents which engage a circumferential groove on the shank. While the balls provide good retention for the shank, they provide poor torque transmission so they are usually found in conjunction with a flat end or other non-circular shank ending which mates with a complementarily shaped driving surface on the shaft. This not only increases the cost of the drills and burs but can also cause delay and confusion during the course of an operation since each different drill requires its own set of cutting tools which are not interchangeable with instruments of other designs.

Ideally, the surgical drill chuck should allow the use of simple low cost drills and burs having straight, non-complex shafts which could be used interchangeably with various power drill designs and which could be economically replaced and/or discarded as they become dulled.

Hedrick U.S. Pat. No. 3,674,281 describes a drill chuck which meets many of these objectives. A plurality of ball elements are frictionally pressed against the drill or bur stem by a wedge shaped sleeve under pressure of a compression spring. The sleeve can be retracted by action of an external manually actuated lever to allow the balls to retract from the drill shaft so that the drill can be removed and replaced. The chuck allows for use of low cost drills and burs having simple shaft designs.

A problem inherent in the design of the Hedrick chuck is the use of spherical balls to establish driving contact with the drill stem. With the use of modern high-torque air motors which provide fast cutting action in dense bone, the point to point contact between chuck and drill stem is inadequate and slippage results in lack of rotation and damage to the drill stem. Also the manually operated release lever is inconveniently located and frequently results in inadvertent release of the bur during crucial times, a problem common to many prior art surgical drill chucks.

Other prior art structures are shown in Hanson U.S. Pat. Nos. 1,582,010; Witt 2,010,210; Sindelar 3,428,327; Herman 3,684,302; Wanner 3,929,343; Bent 3,975,032 and Norlander French Patent No. 961,920.

SUMMARY OF THE INVENTION

The present invention relates to a simple, rugged, compact surgical drill chuck which allows simple low cost drills and burs having straight non-complex shafts to be coupled to a high torque air motor in a slip-proof manner and yet allows for fast replacement of drills or burs without the need for keys, wrenches or other auxiliary tools. A rotary actuated quick release means which requires a certain minimum force to actuate is provided so that the risk of inadvertent release is virtually eliminated.

BRIEF DESCRIPTION OF THE DRAWINGS

In the accompanying drawings which illustrate the invention.

DETAILED DESCRIPTION OF THE INVENTION

Figure 1:
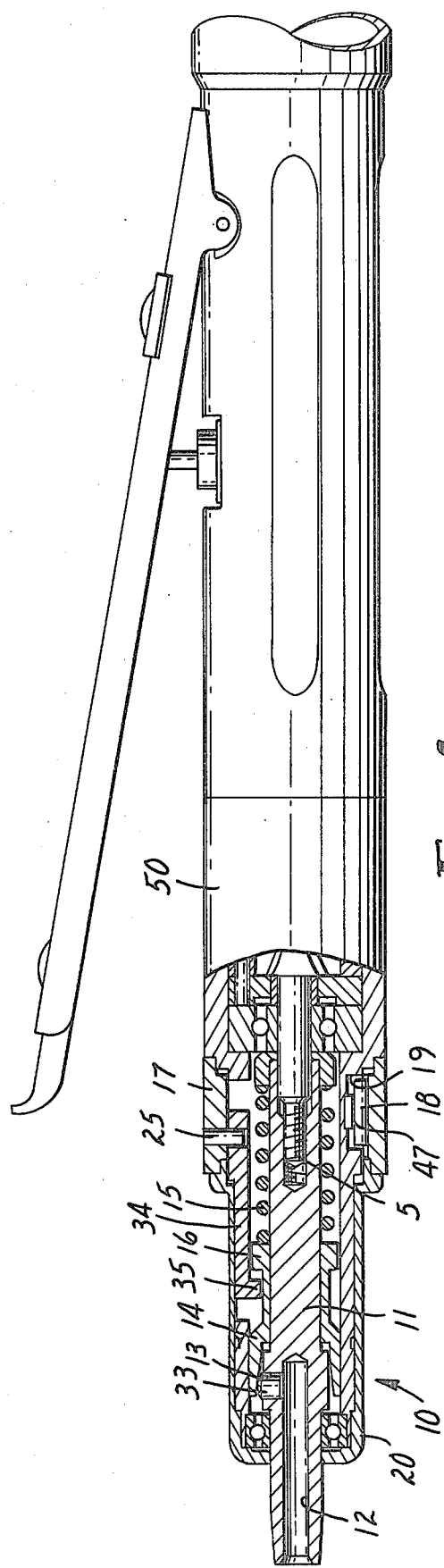
FIG. 1 is a side elevational view of the surgical drill chuck of the present invention mounted onto a surgical drill with parts broken away to better illustrate the same.
Figure 2:
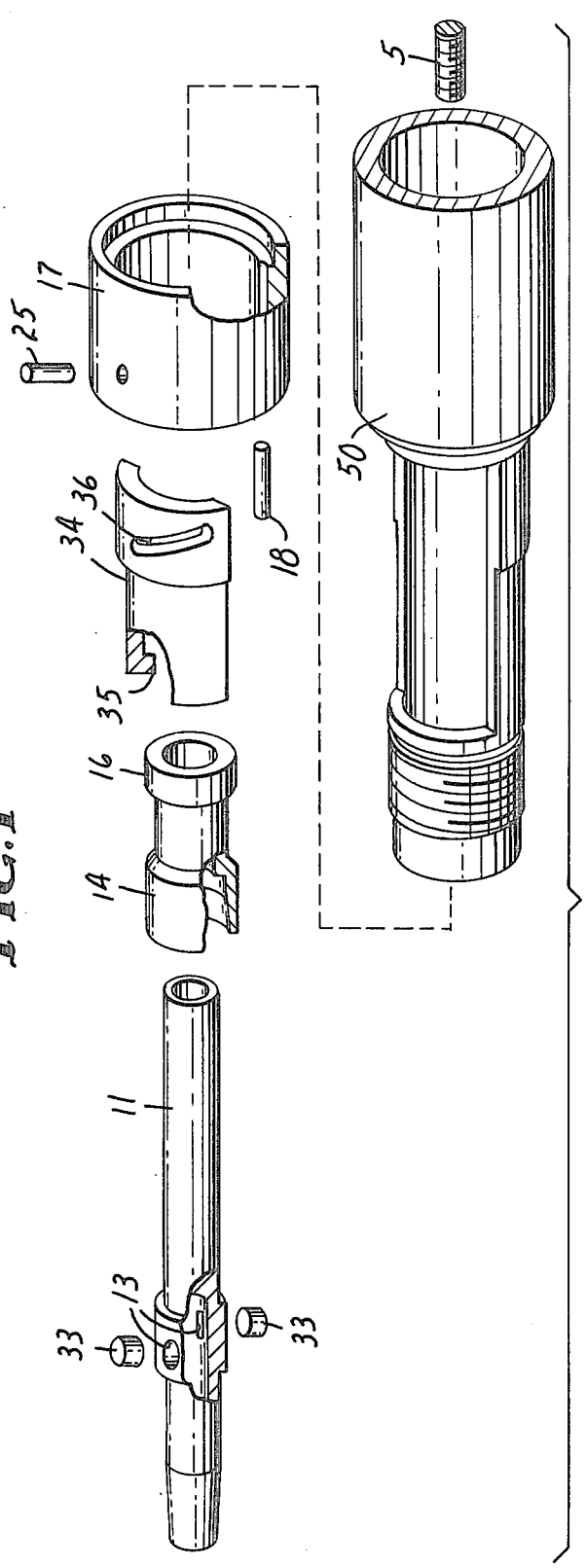
FIG. 2 is an exploded perspective view of the surgical drill chuck of FIG. 1.

Referring now more particularly to the drawings, drill chuck 10 includes spindle 11 which is coupled at one end to the central shaft 5 of an air motor in a conventional manner. Nose cap 20 is fitted over the free end of the spindle in such a manner as to allow spindle 11 to rotate freely therewithin. Spindle 11 has a cylindrical axial bore 12 in said free end, said bore having a controlled internal diameter and being of sufficient depth so that the shafts of interchangeable drills and burs can be accommodated therewithin and supported in firm wobble-free fashion. Adjacent the interior end of bore 12, spindle 11 is provided with a plurality of substantially cylindrical cavities 13 for retaining elements or grippers 33. The cavities are dimensioned such that grippers 33, carried within the cavities, can make line contact with the shaft of a drill or bur inserted within the bore 12 while also restraining the grippers from falling into the bore when no shaft is present. Cavities 13 are generally equidistantly spaced about the circumference of bore 12. Three such cavities have been found to be satisfactory although a greater number could be used. Alternatively, two or more arrays of cavities and grippers could be placed axially along the bore and such arrangements are contemplated.

Retaining elements or grippers 33 are preferably cylindrical and have one substantially flat end so that said end surface will make line contact with a drill or bur stem across its face rather than the point contact provided when spherical retaining elements are used. The other end of gripper 33 is formed as a segment of a sphere so that applied forces will be directed to the center of the spherical surface thereby being transmitted directly normal to the shaft contacting surface. Prismatic shapes other than cylindrical could be used for the grippers.

Applying pressure to the spherical surface of grippers 33 to accomplish torque transmission to the drill or bur shaft is a cylindrical collet closer 14. The forward end (or left end as viewed in FIG. 1) of the collet closer has an internal tapered frusto-conical surface designed to press the grippers inward against the drill or bur shaft when the closer is pressed forward (left) and to release the pressure when the closer is moved rearwardly (to the right). Behind the tapered surface is an internal bore sized to slide axially along the spindle. When the surgical drill chuck is in use on a surgical drill, the collet closer 14 will rotate exactly with the spindle due to the pressure between the drill or bur shaft, the grippers and the collet closer.

The collet closer 14 will normally be held forward (left) through action of biasing means such as a compression spring 15. This spring which will also rotate with the collet closer and the spindle is under considerable compressive pressure to provide the necessary pressure for the grippers.

A slide 34 is provided to pull the collet closer rearwardly (to the right) counter to the biasing means when it is desired to release an engaged drill or bur. Engagement between the slide 34 and the collet closer 14 is provided by a projection 35 on the slide, such as the segmental ridge shown, which can interact with an annular ridge 16 on the collet closer 14. When the drill is being used, the slide 34 will be stationary or non-rotating in contrast to the rotating collet closer 14. It is important therefore that sufficient radial clearance be provided between these two parts so that friction is avoided. Similarly, the slide 34 must be biased directly or indirectly so that axial clearance is provided between the slide projection 35 and the collet closer ridge 16 so that not only is friction eliminated between these two, which could result in undesirable heat, vibration, noise and loss of torque, but to also eliminate rearward force against the collet closer which could cause an inadvertent loss of torque transmitting pressure to the grippers 33 and hence cause slippage of the drill or bur and damage to the drill or bur shaft. The rearward or right end of the slide 34 will preferrably contain a cam surface 36 in the shape of a portion of a helix.

External of the air drill housing 50 and arranged directly within reach of the user's grasp is a release ring 17 having an inwardly projecting key 25 which interacts with the helix shaped cam slot 36 of the slide 34 so that the rotation of the release ring will cause axial movement of the slide. The release ring normally has a knurled or otherwise textured outer surface so that it can be easily grasped and rotated even with wet gloved fingers.

It is normally necessary for the surgeon to use one hand to steady the portion of anatomy upon which he is operating, for example, to steady a child's hand or even a finger. With his other hand, the surgeon must support and direct the drill, control the speed of same and, when frequently necessary, release the dull drill or bur so that another can be inserted. It is thus necessary that all controls, including the release means be conveniently placed within the reach of the user's grasp. Surgical drills known to the prior art usually provided levers, slides or the like to effect release of the gripping means. During intricate surgical procedures, frequently the surgeon would inadvertently activate the release mechanism with sometimes serious results. The flush mounted release ring 17 of the present invention greatly reduces such possibility of inadvertent action but does not totally eliminate the hazard. To further safeguard against inadvertent release and to provide bias to reduce contact between the slide and the collet sleeve, the release ring 17 is retained fully in non-release position by detent means having considerable retention force. Even though the user should use the ring 17 as a gripping surface for the drill 50 while turning or twisting the drill, the detent means will provide sufficient restraint to keep the release ring stationary relative to the drill housing and hence eliminate the possibility of inadvertent actuation of the release mechanism. It is only through deliberate rotation of the release ring 17 relative to the drill body casing 50 that the release mechanism can be actuated, a process requiring a slight change in grip from that normally used to control and direct the drill.

The preferred detent mechanism is a flat leaf spring 47 which fits into a recess in the drill body casing 50 below the release ring 17 and forces a roller 18 into a complementarily shaped recess or groove 19 on the inside of the ring. When the release ring is forcibly turned with a torque greater than 3.25 in.-lb., the roller is dislodged from the groove and the ring can be turned actuating the release mechanism. Alternatively, other detent means may be used such as a spherical ball biased by a helical compression spring within a cylindrical bore, providing that the torque required to dislodge the detent means is within the range of 3.0 to 3.5 in.-lb.

Additional biasing means for either the slide 34 or release ring 17 may be provided but the use of such is superfluous as the release ring 17 will normally be retained in locked position by the detent means 47, 18 except during the brief release periods.

In order to place the present invention in its proper perspective, it is noted that a typical surgical or dental drill with the surgical drill chuck mounted thereon will have a length of about 16.5 cm., a diameter of about 1.7 cm. and weigh about 142 g. A typical operating pressure of such drill would be about 90 to 110 psi at a no load speed of about 50,000 to 60,000 rpm.

I claim:

1. A self-locking, quick release surgical drill chuck for retaining and rotatably driving a drill or bur having a straight, non-complex shank comprising a driven spindle having a cylindrical bore therein for receiving the shank of said drill or bur and having a plurality of cavities spaced about the circumference of said bore and communicating therewith, retaining means comprising a plurality of cylindrical grippers carried in said cavities formed in said spindle and having one substantially flat end for making frictional contact with the shank of a drill or bur in a line along the axis thereof in a first position, the other end of said grippers being a segment of a sphere to enable radial forces applied thereto to be transmitted perpendicularly to said substantially flat shank contacting end and being movable to a second position to permit removal of said shank from and insertion of a new shank therein, said retaining means additionally including a cylindrical collet closer normally biased into pressure-applying engagement with said grippers and slidably carried on said spindle and having an internal frusto-conical bore in one end to permit said collet closer to axially slide over said grippers, said collet closer having an annular ridge at its other end, and a quick release means comprising a rotatable release ring having an inwardly projecting key and a slide having a projection thereon at one end for engagement with the annular ridge on said collet closer and having a helical cam surface at its other end for sliding engagement with said projecting key carried by said release ring such that rotation of said release ring will cause said slide and said collet closer to move axially with respect to said spindle, said release ring being normally biased into a locked position, said biasing means comprising a flat leaf spring and a roller, said release ring having a groove in its interior surface into which said roller is normally biased, said biasing means requiring a force of about 3 in.lb. to overcome the action of said spring and roller against said ring.

* * * * *